US006372466B1

(12) United States Patent
Habuchi et al.

(10) Patent No.: US 6,372,466 B1
(45) Date of Patent: Apr. 16, 2002

(54) C-4 SPECIFIC SULFOTRANSFERASE

(75) Inventors: Osami Habuchi, Nogoya; Shinobu Yamauchi, Seto; Yukie Hirahara, Izumi, all of (JP)

(73) Assignee: Seikagaku Corporation, Tokyo (JP)

( * ) Notice: Subject to any disclaimer, the term of this patent is extended or adjusted under 35 U.S.C. 154(b) by 0 days.

(21) Appl. No.: 09/338,821

(22) Filed: Jun. 23, 1999

(30) Foreign Application Priority Data

Jun. 23, 1998 (JP) ............................................ 10-176447

(51) Int. Cl.$^7$ ................................................. C12N 9/10
(52) U.S. Cl. ........................................ 435/193; 435/183
(58) Field of Search .................................. 435/193, 183

(56) References Cited

PUBLICATIONS

Sugumaran et al., Simultaneous Sulfation of Endogenous Chondroitin Sulfate and Chonfroitin–derived Oligosaccarides, (1986), J.B.C.vol. 261, pp. 12659–12664.*
Habuchi et al., Secretion of Condroitin 6–sulfotransferase and chondroitin 4–sulfotransferase from the cultured chick embryo chondrocytes, (1991), B.B.A. vol. 1133, pp. 9–16.*
Habuchi and Miyashita, Seperartion and Characterization of Chondroitin 6–sulfotransferase and chondroitin 4–sulfotransferase from chick embryo cartilage, (1982), BBA, vol. 717, pp. 414–421.*
Biochimica et Biophysica Acta, *Secretion of chondroitin 6–sulfotransferase and chondroitin 4–sulfotransferase from cultured chick embryo chondrocytes,* 1133 (1991) 9–16, Osami Habuchi, Masafumi Tsuzuki, Ikuko Takeuchi, Masae Hara, Yasuko Matsui and Satoko Ashikari.

O. Habushi, et al. "Stimulation of Glycosaminoglycan from Chick Embryo Cartilage by Basic Proteins and Polyamines." *Biochemica et Biophysica Acta,* 616 (1980), pp. 208–217.

O. Habushi, et al. "Separation and Characterization of Chondroitin 6–Sulfotransferase and Chondroitin 4–Sulfotransferase from Chick Embryo Cartilage." *Biochimica de Biophysica Acta,* 717 (1982) pp. 414–421.

O. Habushi, et al. "Secretion of Chondroitin 6–Sulfotransferase and Chondroitin 4–Sulfotransferase from Cultured Chick Embryo Chondrocytes," *Biochimica et Biophysica Acta,* 1133 (1991) pp. 9–16.

H. Kitagawa, et al. "Developmental Regulation of the Sulfation Profile of Chondroitin Sulfate Chains in the Chicken Embryo Brain." *Journal of Biological Chemistry,* vol. 272, No. 50, Dec., 1997. pp. 31377–31381.

S. Yamauchi, et al. "Purification and Characterization of Chondroitin 4–Sulfotransferase from the Culture Medium of a Rat Chondrosarcoma Cell Line." *The of Biological Chemistry,* vol. 274, No. 4, Jan., 1999, pp. 2456–2463.

S. Yamauchi, et al. "Molecular Cloning and Expression of Chondroitin 4–Sulfotransferase." *Journal of Biological Chemistry,* vol. 275, No. 12, Mar., 2000. pp. 8975–8981.

* cited by examiner

*Primary Examiner*—Jon P. Weber
*Assistant Examiner*—Harry J Guttman
(74) *Attorney, Agent, or Firm*—Knobbe, Martens, Olson & Bear, LLP

(57) ABSTRACT

A galactosaminoglycan 4-sulfotransferase having an activity of transferring a sulfate group from a sulfate group donor to a hydroxyl group at the C-4 position of galactosamine residue of a galactosaminoglycan is presented.

6 Claims, 9 Drawing Sheets

C-4 SPECIFIC SULFOTRANSFERASE

BACKGROUND OF THE INVENTION

The present invention relates to a novel sulfotransferase and more particularly to a galactosaminoglycan sulfotransferase which has an activity of transferring a sulfate group from a sulfate group donor to a hydroxyl group at the C-4 position of a galactosamine residue contained in galactosaminoglycan.

Glycosaminoglycan is a polysaccharide which has a disaccharide unit consisting of an aminosugar residue and an uronic acid residue as a basic skeleton. Such glycosaminoglycan includes, for example, hyaluronic acid, chondroitin, chondroitin 4-sulfate (chondroitin sulfate A), chondroitin 6-sulfate (chondroitin sulfate C), dermatan sulfate (chondroitin sulfate B), keratan sulfate, heparan sulfate and heparin. Of these, those glycosaminoglycans which have a galactosamine residue as the aminosugar residue are called galactosaminoglycan, in which chondroitin, chondroitin sulfate A, chondroitin sulfate C, dermatan sulfate and the like are classified.

Recently, various physiological functions of glycosaminoglycans have attracted attention.

Particularly, it has been being gradually clarified that the amount and position, for example, of sulfate groups which they have are associated with such physiological functions. Thus, the change in physiological activity of glycosaminoglycan due to the change in its sulfate group suggests the possibility that glycosaminoglycan and modifications thereof will be useful as a medicine. Accordingly, research for a sulfotransferase associated with the change in a sulfate group has been promoted, which results in the knowledge of various enzymes which transfer a sulfate group to a specified position of the basic skeleton of glycosaminoglycan, and utilization of such enzymes in the modification of glycosaminoglycan is expected.

Such glycosaminoglycan sulfotransferase includes, for example, chondroitin 6-sulfotransferase (C6ST: transfers a sulfate group from a sulfate group donor to the C-6 position of galactosamine residue; Habuchi, O., Matsui, Y., Kotoya, Y., Aoyama, Y., Yasuda, Y., and Noda, M., (1993) J. Biol. Chem. 268, 21968–21974), haparan sulfate 2-O-sulfotransferase (HS2ST: transfers a sulfate group from a sulfate group donor to the C-2 position of uronic acid residue; Japanese Patent Application Laid-open No. 9-28374 (1997)), heparan sulfate 6-O-sulfotransferase (HS6ST: transfers a sulfate group from a sulfate group donor to the C-6 position of glucosamine residue; Japanese Patent Application Laid-open No. 8-33483 (1996)), and keratan sulfate 6-O-sulfotransferase (KSGal6ST: transfers a sulfate group to the C-6 position of galactose residue; Fukuta, M., Inazawa, J., Torii, T., Tsuzuki, K., Shimada, E., and Habuchi, O. (1997) J. Biol. Chem. 272(51), 32321–32328). However, no enzyme has been isolated that has an activity of transferring a sulfate group to the C-4 position of galactosamine residue of glycosaminoglycan having a galactosamine residue (galactosaminoglycan).

SUMMARY OF THE INVENTION

If only a specified position of the basic skeleton of galactosaminoglycan can be sulfated, then it might be possible to create new galactosaminoglycan that has a physiological activity. It is difficult to sulfate only a specified position by a chemical technique and hence utilization of enzymes is suitable for such a purpose. However, it is only C6ST that has been known as the purified enzyme which can sulfate galactosaminoglycan, so that enzymes that have an activity of transferring a sulfate group to the hydroxyl group at the C-4 position has been expected. Therefore, an object of the present invention is to provide an enzyme which transfers a sulfate group to the hydroxyl group at the C-4 position of galactosamine residue contained in galactosaminoglycan.

With a view to solving the above-mentioned problem, the present inventors have made intensive research and as a result they have now found that galactosaminoglycan 4-sulfotransferase, which transfers a sulfate group to the hydroxyl group at the C-4 position of galactosamine residue contained in galactosaminoglycan, exists in mouse chondrosarcoma cells and further they have been successful in isolating and purifying it, thereby completing the present invention.

That is, the present invention is to provide an isolated galactosaminoglycan 4-sulfotransferase which has an activity of transferring a sulfate group from a sulfate group donor to the hydroxyl group at the C-4 position of galactosamine residue contained in galactosaminoglycan (hereinafter, also referred to as "enzyme of the present invention" or "G4ST").

The enzyme of the present invention preferably acts on chondroitin, chondroitin sulfate A, chondroitin sulfate C, or desulfated dermatan sulfate.

The enzyme of the present invention preferably further has the following properties:
Optimum reaction pH: pH 6.5–7.5;
Enhancement of activity: The activity of the enzyme is enhanced by prolamine or $Ca^{2+}$; and
Inhibition of activity: The activity of the enzyme is inhibited by $Co^{2+}$.

DETAILED DESCRIPTION OF THE INVENTION

Figure 1:
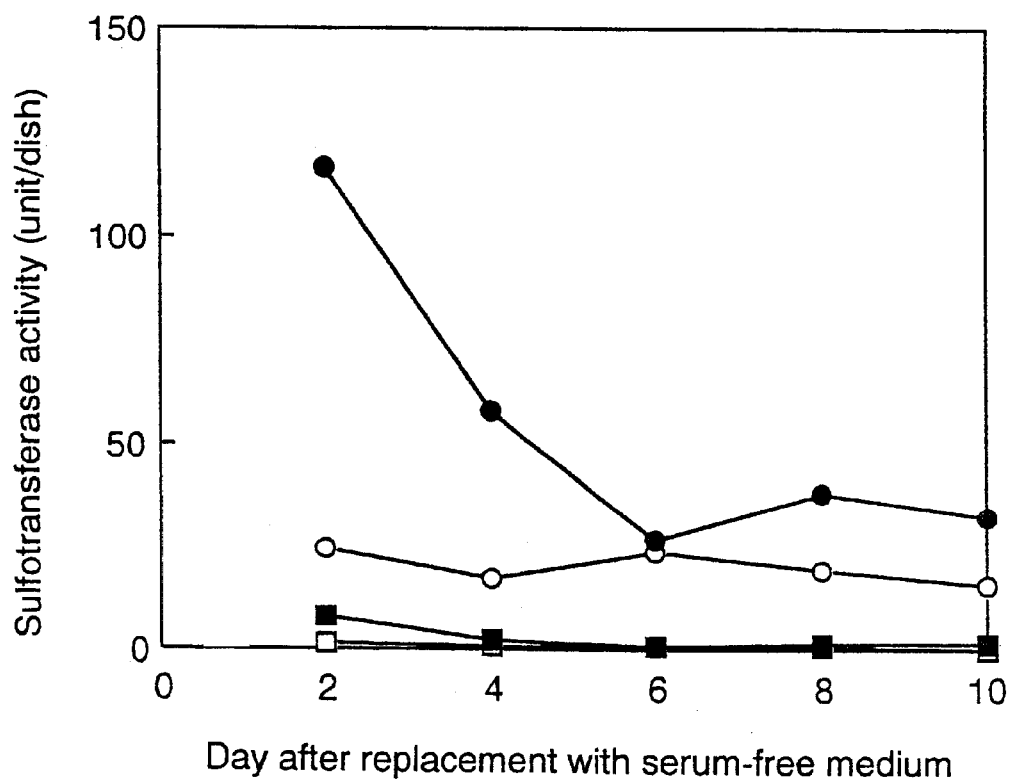
FIG. 1 shows a change in sulfotransferase activity when rat chondrosarcoma cells are cultured in a serum-free medium.

The isolated enzyme of the present invention is galactosaminoglycan 4-sulfotransferase which has an activity of transferring a sulfate group from a sulfate group donor to the hydroxyl group at the C-4 position of galactosamine residue contained in galactosaminoglycan.

The galactosaminoglycan on which the G4ST of the resent invention acts is a glycosaminoglycan which as a galactosamine residue and includes, for example, chondroitin, and dermatan sulfate which has been desulfated (hereafter, referred to as "desulfated dermatan sulfate"). The G4ST of the present invention acts on chondroitin and desulfated dermatan sulfate particularly advantageously.

The sulfate group donor includes activated sulfate (3'-phosphoadenosine 5'-phosphosulfate; hereafter, also referred to as "PAPS").

The G4ST of the present invention typically has any of the following properties (1) to (10), preferably hag the properties (1), (6), (7) and (9) and more preferably has all of the properties (1) to (10) but the present invention is not limited thereto.

(1) Substrate Specificity

It transfers a sulfate group to chondroitin, chondroitin sulfate A, chondroitin sulfate C, and desulfated dermatan sulfate. It transfers substantially no sulfate group to heparan sulfate and CDSNS-heparin (heparin completely desulfated and then N-sulfated);

(2) Molecular Weight

It has a molecular weight of 50 kDa by gel filtration using Toyopearl HW-55 (Tosoh corporation);

(3) Molecular Weight

It has a molecular weight of 60 kDa and 64 kDa by SDS-polyacrylamide gel electrophoresis under reducing conditions;

(4) Molecular Weight

It has a molecular weight of 50 kDa and 54 kDa by SDS-polyacrylamide gel electrophoresis under non-reducing conditions;

(5) Molecular Weight

It has a molecular weight of 33 kDa and 35 kDa by SDS-polyacrylamide gel electrophoresis under non-reducing conditions after N-glycanase treatment;

(6) Optimum Reaction pH

It has high sulfotransferase activity in a reaction mixture at a pH in the range of 6.5 to 7.5, particularly at a pH about 7.2. It has substantially no activity at pH 4.0 or less;

(7) Enhancement of Activity

The activity of the enzyme is enhanced by protamine (0.25 mg/ml) or $Ca^{2+}$ (5 m);

(8) Enhancement of Activity

The activity of the enzyme is enhanced by at least one ion (5 mM) selected from the group consisting $Fe^{2+}$, $Mn^{2+}$, $Ba^{2+}$ and $Sr^{2+}$; and (9) Inhibition of Activity The activity of the enzyme is inhibited by $Co^{2+}$ (5 mM).

(10) Km Value (for PAPS): $2.7 \times 10^{-7}$ M

Each of the above-mentioned properties can be determined by the methods described in the examples described hereinbelow.

Next, the production method for G4ST will be explained below.

As will be shown in the examples described below, G4ST has been isolated from a culture supernatant of rat chondrosarcoma cell and the properties thereof has been elucidated for the first time by the present invention. Since the properties of G4ST has been clarified, use of the properties as indices enables one to easily select a starting material and purification conditions for the production of G4ST.

Examples of the starting material includes tissues or cells of mammalians and avians in which chondroitin sulfate distributes abundantly, their cultured cells as well as supernatant of cultures. Preferably, cells or cartilage are cited. In particular, rat chondrosarcoma cells are preferred since their culture supernatant contains much more G4ST than C6ST.

Purification from the starting materials can be conducted according to isolation and purification methods for sulfotransferases which methods are known per se.

Further, if a gene is obtained which codes for whole or a part of the G4ST of the present invention from the above-mentioned cells or the like based on the amino acid sequence of purified G4ST, it is possible to produce the enzyme of the present invention by ligating the gene to a suitable vector, introducing the vector in other cell or microorganisms, and culturing them.

Therefore, the origin and production method of G4ST of the present invention is not limited particularly so long as it is an enzyme which has the above-mentioned activity.

The production method for G4ST according to the present invention includes the following method, for example.

<1> Preparation of Supernatant of Cell Culture

C Cells or cultured cells containing G4ST, originating from a tissue of mammalian or avian, for example chondrosarcoma cells or the like are cultured in a suitable medium, for example, Dulbecco's modified Eagle's medium (manufactured by Gibco BRL) and Cosmedium-001 (manufactured by Cosmo-Bio Co., Ltd.) and the culture supernatant is recovered and pooled. To promote the growth of cells, the cells are cultured in a serum-containing medium such as Dulbecco's modified Eagle's medium containing fetal bovine serum or the like at the time when culture is started and the culture is then continued by exchanging the medium with a medium for purifying G4ST (this medium is preferably a serum-free medium, for example, the above-mentioned Cosmedium-001 or the like, from the viewpoint of simplicity of subsequent purification and so on). When the culture supernatant is pooled, it is preferred that a measure be taken to secure the stability of G4ST; for example, pH is adjusted to about 6 to 8, preferably 6.5 to 7.5, by use of a suitable buffer (preferably Tris-HCl) and Triton X-100, $MgCl_2$, 2-mercaptoethanol, glycerol, a protease inhibitor (for example, $N^{\alpha}$-p-tosyl-L-lysine chloromethyl ketone, N-tosyl-L-phenylalanine chloromethyl ketone, phenylmethylsulfonyl fluoride, pepstatin A), or the like is added. It is preferred that the pooled culture supernatant is stored at 4° C.

<2> Purification of G4ST by Chromatography

Purification of G4ST can be carried out by a combination of generally used affinity chromatography and gel chromatography under the conditions usually used for the purification of enzymes (for example, 4° C.). For example, purification of G4ST can be performed by an appropriate combination of (1) affinity chromatography using a heparin-Sepharose column CL-6B (manufactured by Pharmacia LKB Biotechnology Co.), (2) affinity chromatography using a Matrex Gel Red A column (manufactured by Amicon Co.), and (3) affinity chromatography using a 3',5'-ADP-agarose gel (manufactured by Sigma Aldrich Co.). Hereafter, an example of such a purification method will be explained.

(1) Affinity Chromatography using Heparin-Sepharose Column

To a heparin-Sepharose column equilibrated with a buffer containing NaCl (0.15 M) is applied the medium recovered in <1> above, and the substance adsorbed on the column is eluted with a buffer containing NaCl (0.4 M). The activity of the enzyme is monitored, for example, by use of the method described in Habuchi, O., Matsui, Y., Kotoya, Y., Aoyama, Y., Yasuda, Y., and Noda, M., (1993) J. Biol. Chem. 268, 21968–21974) and fractions showing high G4ST activity are recovered.

(2) Affinity Chromatography using Matrex Gel Red A Column

The fractions obtained in (1) above are mixed and applied to a Matrex Gel Red A column equilibrated with a buffer containing NaCl (0.4 M) and eluted with a buffer containing NaCl (0.4 M) and then with a buffer containing NaCl (0.75 M) and a buffer containing quanidine hydrochloride (1 M). The activity of G4ST is monitored, fractions of which G4ST activity is confirmed are recovered, and the fractions are dialyzed against a buffer containing NaCl (0.05 M) to remove guanidine hydrochloride. It is preferred that a surfactant such as Triton X-100 be added to the inner dialyzed solution.

(3) Affinity Chromatography using 3',5'-ADP-agarose Gel

The dialyzed solution obtained in (2) above is applied to a 3',5'-ADP-agarose gel column equilibrated with a buffer containing NaCl (0.05 M) (containing a surfactant), and eluted with a buffer containing 3',5'-ADP (containing a surfactant), and fractions having a G4ST activity are recovered.

(4) Affinity Chromatography using Heparin-Sepharose CL-6B Column

The fractions obtained in (3) above are overlaid on a heparin-Sepharose column equilibrated with a buffer containing NaCl (0.05 M), and eluted with a buffer containing NaCl (0.4 M). Recovered adsorbed fractions are dialyzed against a buffer containing NaCl (0.05 M).

It is considered that one skilled in the art can practice a further simplified purification method based on the above-exemplified purification method by appropriately applying or modifying it.

For example, the following method may be cited. Cultured cells are subjected to a physical extraction method (extraction methods such as a method using a homogenizer, a glass bead mill method, a freezing-thawing method, an ultrasonic disruption method, and an osmotic pressure shock method) or a chemical extraction method (for example, an extraction method using a surfactant) to prepare an extract, or a culture supernatant is prepared by recovering the medium used when the cells are cultured. Then, G4ST is purified from the extract or the culture supernatant by treatment operations such as salting out with ammonium sulfate or the like, centrifugation, dialysis, ultrafiltration, adsorption chromatography, ion exchange chromatography, hydrophobic chromatography, reverse phase chromatography, gel filtration, gel permeation chromatography, affinity chromatography or electrophoresis or a combination of two or more of these.

By the present invention, there is provided a galactosaminoglycan 4-sulfotransferase having an activity of transferring a sulfate group from a sulfate donor to the hydroxyl group at the C-4 position of galactosamine residue of galactosaminoglycan.

EXAMPLES

The present invention will now be described in more detail by way of non-limiting illustrative examples. An assay method commonly used to all the examples is explained at the beginning.

The activities of G4ST and C6ST were assayed in accordance with the method of Habuchi, O. et al. (Habuchi, O., Matsui, Y., Kotoya, Y., Aoyama, Y., Yasuda, Y., and Noda, M., (1993) J. Biol. Chem., 268, 21968–21974). The reaction mixture contained imidazole hydrochloride (2.5 $\mu$mol, pH 6.8), protamine chloride (1.25 $\mu$g), dithiothreitol (0.1 $\mu$mol), chondroitin (25 nmol as glucuronic acid, derived from squid skin, prepared by the method described in Habuchi, O. and Miyata, K. (1980) Biochim. Biophys. Acta 616, 208–217), [$^{35}$S]PAPS (50 pmol: about $5.0 \times 10^5$ cpm: prepared by the method of Delfert, D. M., et al. (Delfert, D. M., and Conrad, H. E. (1985) Anal. Biochem. 148, 303–310)) and an enzyme in a final volume of 50 $\mu$l.

The above-mentioned reaction mixture was incubated at 37° C. for 20 minutes and immersed in a water bath kept at 100° C. for 1 minute to stop the enzymatic reaction. After the reaction was stopped, [$^{35}$S]-labeled chondroitin was isolated by desalting by gel chromatography using a Fast Desalting Column and precipitation with ethanol, and radioactivity was measured by the conventional manner.

To distinguish the activities of C6ST and G4ST one from another, [$^{35}$S]-labeled chondroitin was digested with chondroitinase ACII and unsaturated disaccharides (ΔDi-4S (2-acetamide-2-deoxy-3-O-(β-D-gluco-4-enepyranosyluronic acid)-4-O-sulfo-D-galactose) and ΔDi-6S (2-acetamide-2-deoxy-3-O-(β-D-gluco-4-enepyranosyluronic acid-6-O-sulfo-D-galactose)) were separated by paper chromatography (filter paper: Toyo No. 51A and solvent: 1-butanol/acetic acid/NH$_3$ (1 M) (volume ratio 2:3:1)), the separated unsaturated disaccharides were visualized by irradiation of ultraviolet rays, the regions containing the disaccharides were cut out, and then radioactivities thereof were counted.

The amount of enzymatic activity required for transferring 1 pmol of a sulfate group for 1 minute under the conditions of 37° C. and pH 6.8 was defined as one unit as a unit of enzymatic activity.

<1> Culture of Rat Chondrosarcoma Cells and Preparation of the Medium Fraction (1) Culture of Rat Chondrosarcoma Cells Rat chondrosarcoma cells (frozen cell line: LTC) (Midura, R. J., Calabro, A., Yanagishita, M., and Hascall, V. C. (1995) J. Biol. Chem. 270, 8009–8015) were plated in culture dishes of 10 cm in diameter (manufactured by Falcon Co.) at a density of $2 \times 10^6$ cells per dish. The medium (10 ml per dish) used for culture of the cells was a Dulbecco's modified Eagle's medium (pH 7.4; manufactured by Gibco BRL Co.) which contained penicillin (100 units/ml), streptomycin (50 $\mu$g/ml), 5% fetal bovine serum, and insulin (5 $\mu$g/ml) and the culture was carried out under the conditions of 37° C., 5% $CO_2$, and 95% air. The medium was changed at every other days. At the time when the cell grew to the confluent, the cells were treated with Hanks' solution containing trypsin (0.1%) and collagenase (0.1%) (manufactured by Nissui Seiyaku Co., Ltd.), replated in 200 culture dishes of 10 cm in diameter at a density of $2.0 \times 10^5$ cells per dish using the above-mentioned medium, and cultured. On the 6th day when the cell density reached $5.2 \times 10^6$ cells per dish, the medium was replaced with Cosmedium-001 (manufactured by Cosmo Bio Co., Ltd.). The culture of chondrosarcoma cells in Cosmedium-001 was continued for additional 4 days and the spent medium was recovered on the second and fourth days. The culture of chondrosarcoma cells in two hundreds (200) 10-cm culture dishes was repeated three times and then the mediums were recovered.

(2) Preparation of Culture Supernatant

The recovered mediums were centrifuged at 10,000×g for 10 minutes. To the supernatant fraction obtained by the centrifugation were added Tris-HCl (final concentration: 10 mM, final pH: 7.2), Triton X-100 (final concentration: 0.1%), $MgCl_2$ (final concentration 20 mM), 2-mercaptoethanol (final concentration: 10 mM), glycerol (final concentration: 20%), and a mixed solution of protease inhibitors ($N^\alpha$-p-tosyl-L-lysine chloromethyl ketone (final concentration: 5 $\mu$M), (N-tosyl-L-phenylalanine chloromethyl ketone (final concentration: 3 $\mu$M), phenylmethylsulfonyl fluoride (final concentration: 30 $\mu$M), and pepstatin A (final concentration: 3 $\mu$M)). The recovered medium containing the above-mentioned additives was stored at 4° C. as "buffered culture supernatant" until purification was started.

(3) Assay of G4ST Activity During Culture Period

The G4ST activity and C6ST activity in the culture supernatant and cell extract were assayed for 10 days after the replacement with a serum-free medium (Cosmedium-001) (FIG. 1). The culture supernatant was prepared according to (2) above, and the cell extract was prepared according to the following method. Cells were separated from the culture dish in Tris-HCl (0.01 M) at pH 7.2 containing sucrose (0.25 M) and Triton X-100 (0.01 M), homogenized using a Downs homogenizer, and then centrifuged at 10,000×g for 20 minutes to obtain a supernatant fraction, and the fraction was used as a cell extract.

The assay of G4ST activity demonstrated that the G4ST activity in the serum-free medium decreased abruptly; the G4ST activity decreased to 48% of the initial G4ST activity after 4 days (closed circles in FIG. 1) whereas the G4ST activity of cells remained substantially the same level throughout the culture period (open circles in FIG. 1).

Unlike C6ST obtained from known chick chondrosarcoma cells (Habuchi, O., Tsuzuki, M., Takeuchi, I., Hara, M., Matsui, Y., and Ashikari, S. (1991) Biochem. Biophys. Acta 1133, 9–16), secretion of G4ST in the medium was not promoted by addition of ascorbic acid. Throughout the whole culture period, a slight amount of C6ST activity was observed in both the medium and cells (closed squares and open squares in FIG. 1).

<2> Purification of Galactosaminoglycan 4-sulfotransferase

All of the following steps were perfomed at 4° C.

(1) Chromatography using Heparin-Sepharose CL-6B Column

To a heparin-Sepharose CL-6B column (2.2×28 cm: manufactured by Pharmacia) equilibrated with buffer A (which contains Tris-HCl (10 mM, pH 7.2), $MgCl_2$ (20 mM), $CaCl_2$ (2 mM), 2-mercaptoethanol (10 mM), Triton X-100 (0.1%) and glycerol (20%)) containing NaCl (0.15 M) was applied the "buffered culture supernatant" (4.7 liters obtained from two hundreds 10-cm dishes) prepared in <1>-(2) above. The above-mentioned column was washed with 1 liter of buffer A containing NaCl (0.15 M) and the materials adsorbed on the column were eluted with 1 liter of buffer A containing NaCl (0.4 M). The column chromatography using heparin-Sepharose CL-6B was performed three times and the obtained fractions containing 0.4 M NaCl were combined.

(2) Chromatography using Matrex Gel Red A Column

Half the total amount of the combined fractions obtained in (1) above was applied to a Matrex Gel Red A column (2.2×9.5 cm: manufactured by Amicon Co.) equilibrated with buffer A containing NaCl (0.4 M). This column was eluted stepwise with 200 ml of buffer A containing NaCl (0.4 M), 200 ml of buffer A containing NaCl (0.75 M), and 200 ml of buffer A containing guanidine hydrochloride (1 M) in order. All of G4ST activity was confirmed in fractions eluted with 1 M guanidine hydrochloride. All the fractions that have G4ST activity were recovered, mixed and dialyzed against buffer A containing NaCl (0.05 M). Chromatography using a Matrex Gel Red A was repeated once again and the dialyzed solutions were combined. To the combined solution was added Triton X-100 (10%) to a final concentration of 2%.

(3) Chromatography using 3',5'-ADP-agarose Gel

The dialyzed solution containing Triton X-100 (2%) obtained in (2) above was applied to a 3',5'-ADP-agarose column (1.2×11 cm: manufactured by Sigma-Aldrich Co.) equilibrated with a modified buffer A containing NaCl (0.05 M) (the above-mentioned buffer A further containing 2% Triton X-100). The column, after washing with 150 ml of the modified buffer A containing NaCl (0.05 M), was eluted with 150 ml of the modified buffer A containing 3',5'-ADP (0.1 mM). G4ST activities in the eluted fractions were determined and then the fractions having a G4ST activity were collected and combined.

Figure 2:
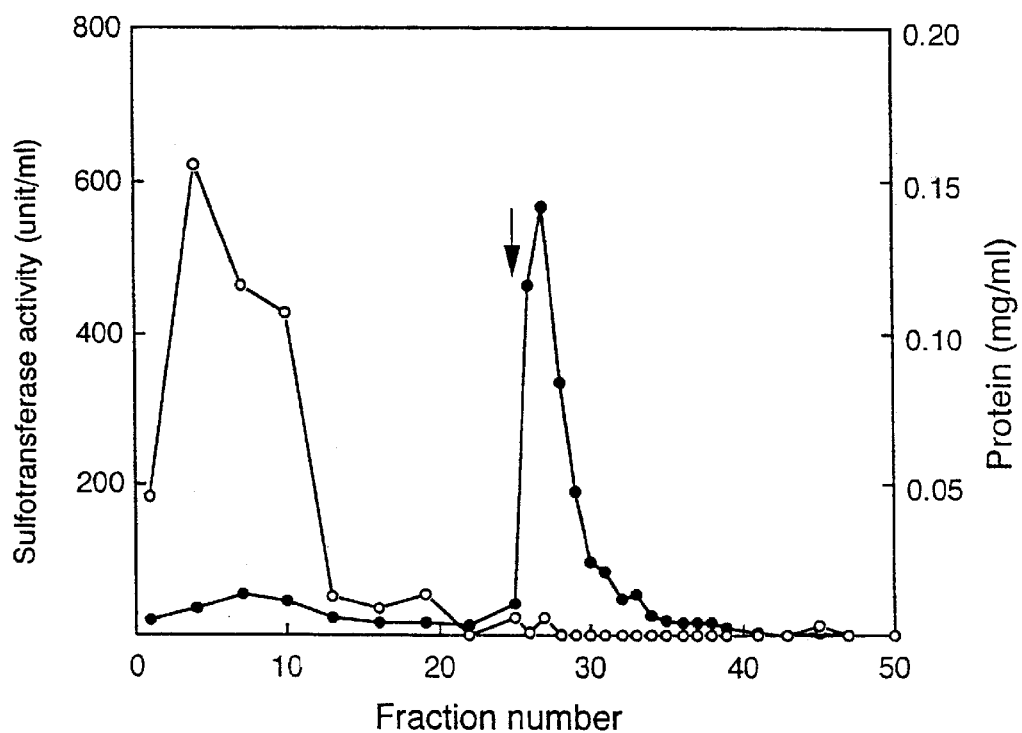
FIG. 2 shows results of affinity chromatography by use of a 3',5'-ADP-agarose column in a purification step.

FIG. 2 illustrates an elution curve of G4ST eluted from the 3',5'-ADP-agarose column and the arrow indicates the start of elution with a modified buffer A containing 0.1 mM 3',5'-ADP. In FIG. 2, closed miracles indicate G4ST activity and open circles indicate the concentration of a protein.

(4) Chromatography using Second Heparin-Sepharose CL-6B Column

The combined fraction containing G4ST obtained in (3) above was applied to a heparin-Sepharose CL-6B column (0.9×6.7 cm) equilibrated with buffer A containing NaCl (0.05 M) and the column was washed with 50 ml of buffer A containing NaCl (0.05 M). The sulfotransferase adsorbed on the column was eluted with 25 ml of buffer A containing NaCl (0.4 M). The recovered fractions were dialyzed against buffer A containing NaCl (0.05 M) and the resultant purified G4ST was stored at −20° C.

<3> Specific Activity in each Purification Step

Specific activity in each purification step was measured and used as an index for the purification of G4ST (Table 1).

TABLE 1

| Purification Step | Total Volume ml | Total Activity $10^{-4}$ × unit | Total Protein mg | Specific Activity $10^{-5}$ × unit/mg Protein | Purification Fold |
|---|---|---|---|---|---|
| Buffered Culture Supernatant | 14,200 | 29.7 | 984 | 0.003 | 1.0 |
| Heparin-Sepharose CL-6B | 950 | 15.9 | 76.0 | 0.021 | 7.0 |
| Matrex Gel Red A | 195 | 13.9 | 39.8 | 0.035 | 11.7 |
| 3',5'-ADP-Agarose | 61 | 3.8 | ND | ND | ND |
| Second Heparin-Sepharose CL-6B | 25 | 1.8 | 0.031 | 5.8 | 1920 |

ND: Not determined

In the purification from the buffered culture supernatant obtained in <1>-(2) above, G4ST obtained in <2>-(4) above was purified to 1,900 folds or more in specific activity. Table 1 shows the degree of purification in each step of G4ST purification from 14.2 liters of the buffered culture supernatant. Measurement of the amount of protein was practiced by the method described in Bradford, M. (1976) Anal. Biochem. 72, 248–254 using bovine serum albumin as a standard. Since the concentration of protein in the fractions obtained using the second heparin-Sepharose CL-6B was below the detection limit, so that the fractions were concentrated by the method described in Habuchi, O., Matsui, Y., Kotoya, Y., Aoyama, Y., Yasuda, Y., and Noda, M., (1993) J. Biol. Chem., 268, 21968–21974). The reason why in Table 1 the concentration of protein in the fractions by chromatography using a 3',5'-ADP-agarose gel is marked as "not determined (ND)" is that the Triton X-100 in the obtained fractions was in high concentrations and therefore it was impossible to measure the accurate amount of protein.

<4> Determination of Substrate Specificity

According to the measurement method for enzymatic activity described above, the activity of G4ST of transferring a sulfate group to glycosaminoglycans other than chondroitin was measured. A reaction mixture used as a control of reaction was the reaction mixture described for the above-mentioned assay method for enzymatic activity (imidazole hydrochloride (2.5 μmol, pH 6.8), protamine chloride (1.25 μg), dithiothreitol (0.1 μmol), chondroitin (25 nmol as glucuronic acid), [$^{35}$S]PAPS (50 pmol: about 5.0×

10⁵ cpm), and an enzyme, total volume 50 μl) and the activity was measured by replacing the chondroitin contained in the above-mentioned reaction mixture as a control with (1) chondroitin sulfate A (derived from whale cartilage) (manufactured by Seikagaku Corp.), chondroitin sulfate C (derived from shark cartilage) (manufactured by Seikagaku Corp.), and chondroitin sulfate E (derived from squid cartilage) (prepared by the method described in Habuchi, O., Sugiura, K., Kawai, N. and Suzuki, S. (1977) J. Biol. Chem. 252, 4570–4576), (2) dermatan sulfate (derived from pig skin) (manufactured by Seikagaku Corp.), (3) desulfated dermatan sulfate (prepared by the method described by Nagasawa, et al. (Nagasawa, K., Inoue, Y., and Tokuyasu, T. (1995) J. Biochem. 86, 1323–1329)), (4) heparan sulfate (derived from bovine kidney) (manufactured by Seikagaku Corp.), (5) CDSNS-heparin (completely desulfated N-sulfated heparin: manufactured by Seikagaku Corp.), and (6) keratan sulfate (derived from bovine cornea) (manufactured by Seikagaku Corp.) ((1), (2) and (3) were each in an amount of 25 nmol as galactosamine, while (4), (5) and (6) were each in an amount of 25 nmol as glucosamine).

As a result, it revealed that G4ST transfers a sulfate group to desulfated dermatan sulfate as well as to chondroitin. It showed a slight amount of activity to chondroitin sulfate A and chondroitin sulfate C was able to be a receptor substrate. It transferred substantially no sulfate group to dermatan sulfate, keratan sulfater chondroitin sulfate E, heparan sulfate and CDSNS-heparin.

<5> SDS-Polyacrylamide Gel Electrophoresis

SDS-Polyacrylamide gel electrophoresis for the analysis of proteins was performed by the method described in Laemmli, U. K. (1970) Nature 227, 680–685 under reducing and non-reducing conditions using 10% polyacrylamide gel. The bands of protein were detected by silver staining and Coomassie-Brilliant Blue staining.

Figure 3:
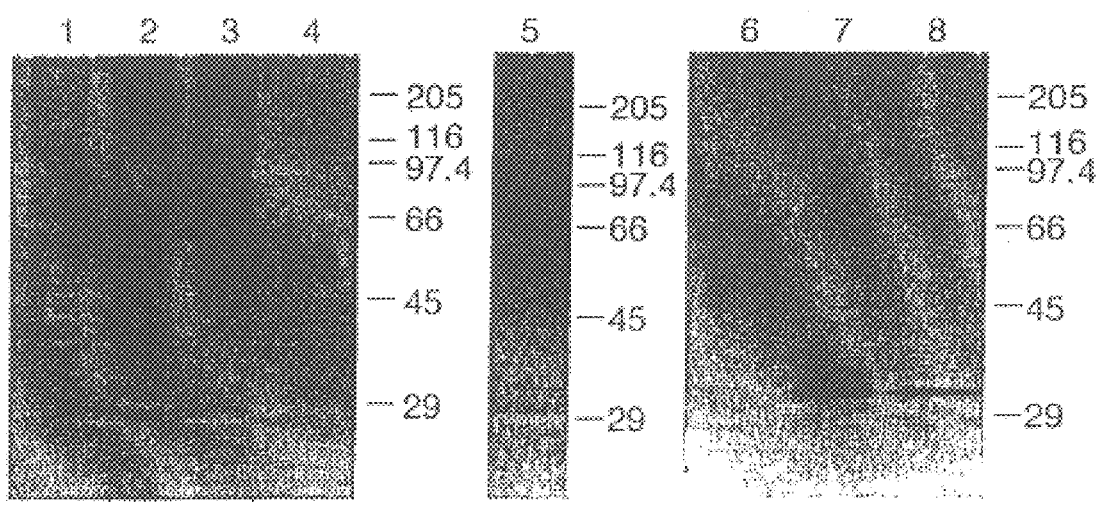
FIG. 3 shows results of analysis by SDS-polyacrylamide gel electrophoresis of fractions in respective purification steps and of purified G4ST.

The protein in each step of G4ST purification was analyzed by SDS-polyacrylamide gel electrophoresis under non-reducing conditions and silver staining method (FIG. 3, Lane 1 (buffered culture supernatant (<1>-(2))), Lane 2 (Heparin-Sepharose CL-6B column (<2>-(1))), Lane 3 (Matrex Gel Red A column (<2>-(2))), and Lane 4 (second Heparin-Sepharose CL-6B column (<2>-(4))). In the fractions eluted from the second Heparin-Sepharose CL-6B column, a clear, broad 50 kDa band of protein appeared and a thin 54 kDa band was also detected (FIG. 3, Lane 4). Also, the purified G4ST (<2>-(4)) was subjected to SDS-polyacrylamide gel electrophoresis under reducing conditions and Coomassie-Brilliant Blue staining, two bands of 60 kDa and 64 kDa were detected (FIG. 3, Lane 5). Also, the purified G4ST (<2>-(4)) and a N-glycanase (manufactured by Genzyme Co.)-digested product of the purified G4ST were subjected to SDS-polyacrylamide gel electrophoresis under non-reducing conditions and compared (G4ST: FIG. 3, Lane 6; N-glycanase-digested G4ST: FIG. 3, Lane 7). The broad 50 kDa band and thin 54 kDa band observed in G4ST each disappeared and a thick 33 kDa band and a thin 35 kDa band were newly observed, which suggested that the purified protein would contain a N-linked oligosaccharide. Lane 8 in FIG. 3 shows the results of analysis of N-glycanase alone under non-reducing conditions as a control.

<6> Gel Chromatography of G4ST using a Toyopearl HW-55 Column

Figure 4:
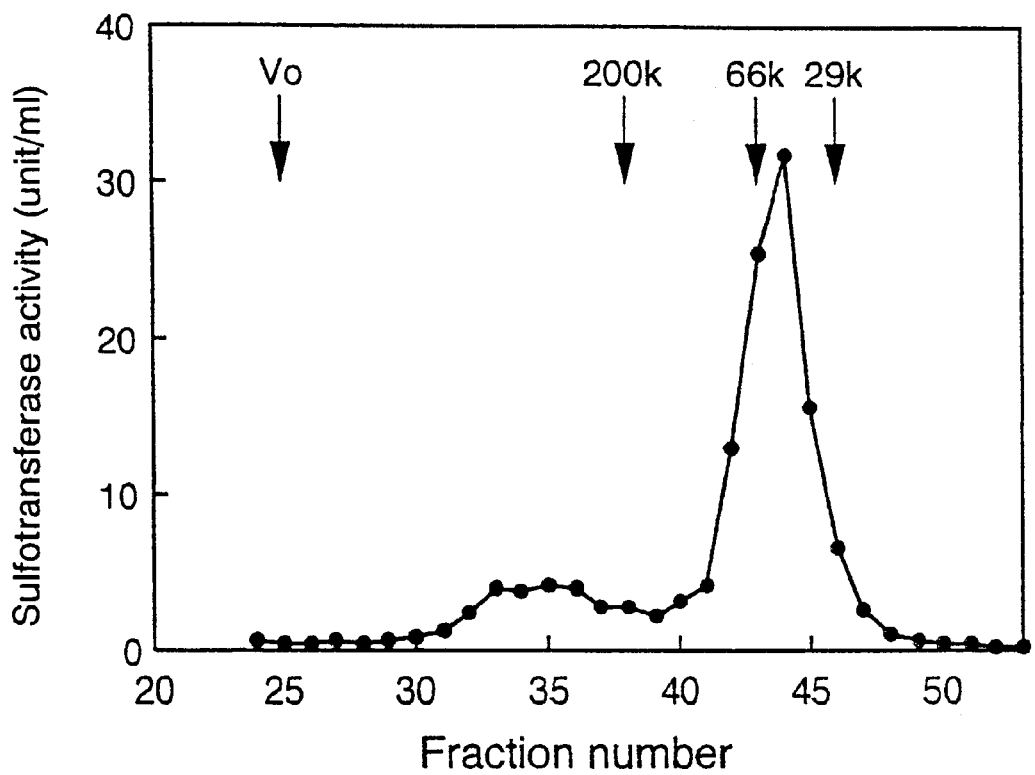
FIG. 4 shows results of chromatography by use of Toyopearl HW-55 gel.

To a Toyopearl HW-55 column (1.4×99 cm: manufactured by Tosoh Corp.) equilibrated with buffer B (which contained Nacl (2 M), Tris-HCl (10 mM, pH 7.2), MgCl₂ (20 mM), CaCl₂ (2 mM), Triton X-100 (0.1%) and glycerol 20%)), 0.8 ml of sample was applied and eluted with buffer B, to recover 1.2 ml each of the eluted fractions, and measured for G4ST activity (FIG. 4). The indication by the arrows corresponds to elution positions of β-amylase (200 kDa), bovine serum albumin (66 kDa) and carbonic anhydrase (29 kDa).

From the elution time of Toyopearl HW-55 chromatography, the molecular weight of G4ST was calculated to be 50 kDa.

Figure 5:
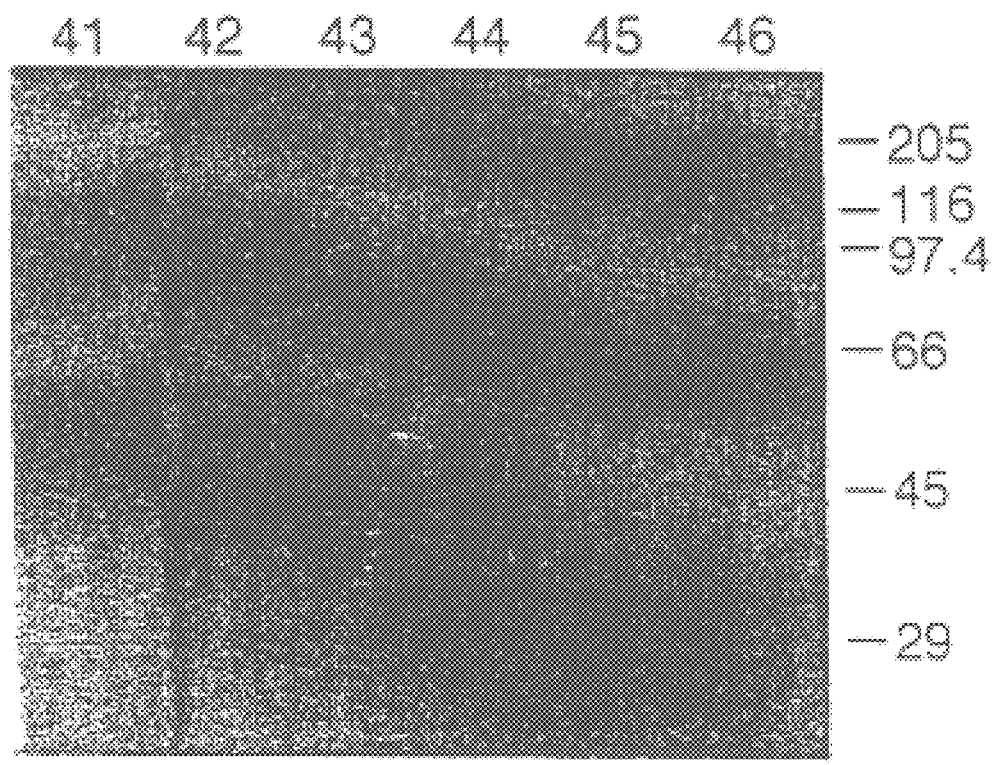
FIG. 5 shows results of analysis by SDS-polyacrylamide gel electrophoresis of protein contained in fractions Nos. 41 to 46 by use of Toyopearl HW-55 gel.

Further, the proteins contained in the fractions of Fraction Nos. 41 to 46 near the maximum peak in FIG. 4 were treated with trichloroacetic acid (10%) to form precipitates. The precipitates were washed with acetone and then subjected to SDS-polyacrylamide gel electrophoresis under non-reducing conditions and detected by silver staining method (FIG. 5). As a result, 50 kDa and 54 kDa bands were detected in Fraction Nos. 43 to 44.

<7> Properties of Enzyme (1) Enhancement and Inhibition of Activity

Figure 6:
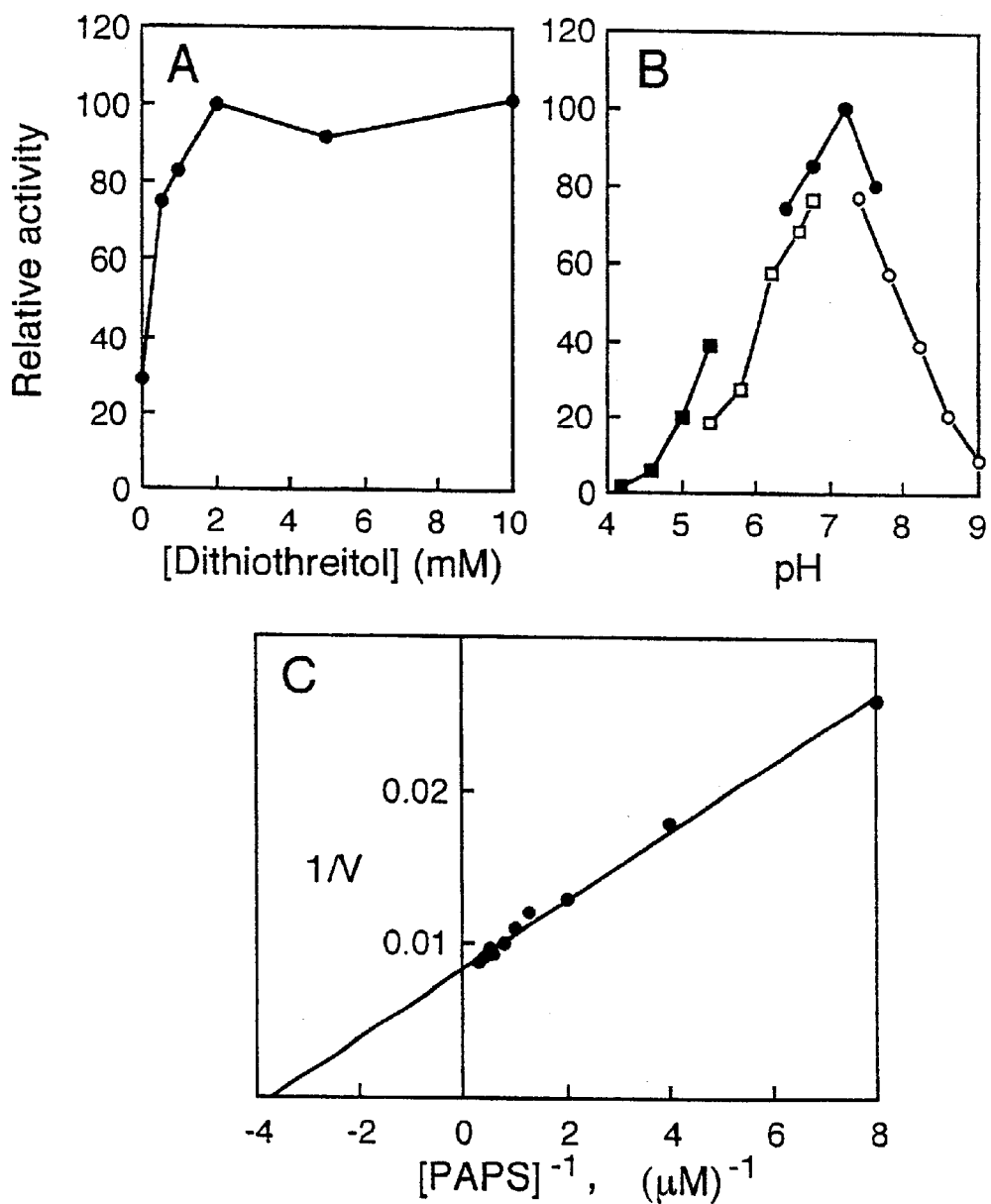
FIG. 6 shows properties of G4ST.

In the above-mentioned assay method for enzymatic activity, the assay of G4ST activity with varying the concentration of dithiothreitol contained in the reaction mixture demonstrated that dithiothreitol enhanced the activity of G4ST (FIG. 6A). Also, assay of the activity of other SH group-containing substances on the G4ST activity using the same assay method for enzymatic activity in the same manner as described above demonstrated that 2-mercaptoethanol or reduced glutathione enhanced the G4ST activity.

Further, it was also demonstrated that the enzyme was activated with protamine (0.25 mg/ml) and a metal ion such as $Ca^{2+}$ (5 mM), $Fe^{2+}$ (5 mM), $Mn^{2+}$ (5 mM), $Ba^{2+}$ (5 mM) or $Sr^{2+}$ (5 mM). The activity of G4ST was most activated particularly when 5 mM $Ca^{2+}$ was added. $Mg^{2+}$ was the lowest in such an activating action. $Co^{2+}$ (5 mM, which wag known to activate C6ST, was demonstrated to inhibit the activity of G4ST.

(2) Optimum Reaction pH

Also, in the above-mentioned assay method for enzymatic activity, pH of imidazole hydrochloride buffer in the reaction mixture was varied (pH range: 6.3 to 7.6) and in addition, the buffer was replaced by one of buffers having various pH ranges (0.05 M, acetate buffer: pH 4.2 to 5.4, MES buffer: pH 5.4 to 6.8, Tris-HCl buffer: pH 7.2 to 9.0), and G4ST activity was assayed at each pH range (FIG. 6B). The results demonstrated that G4ST showed a high activity in the range of pH 6.5 to 7.5, particularly it showed the highest activity about pH 7.2 (FIG. 6B).

(3) Km Value

In the above-mentioned assay method for enzymatic activity, the concentration of [³⁵S]PAPS in the reaction mixture was varied to measure the Km value of [³⁵S]PAPS as a sulfate group donor. The results demonstrated that PAPS had a Km value of $2.7 \times 10^{-7}$ M (FIG. 6C).

(4) Stability of the Enzyme

The purified G4ST was demonstrated to have a low stability as compared with C6ST derived from culture supernatant of chick chondrocytes. When stored at −20+ C. for 4 months, the activity of G4ST decreased by about 20% as compared with the activity before the storage.

(5) Substrate Specificity

Figure 7:
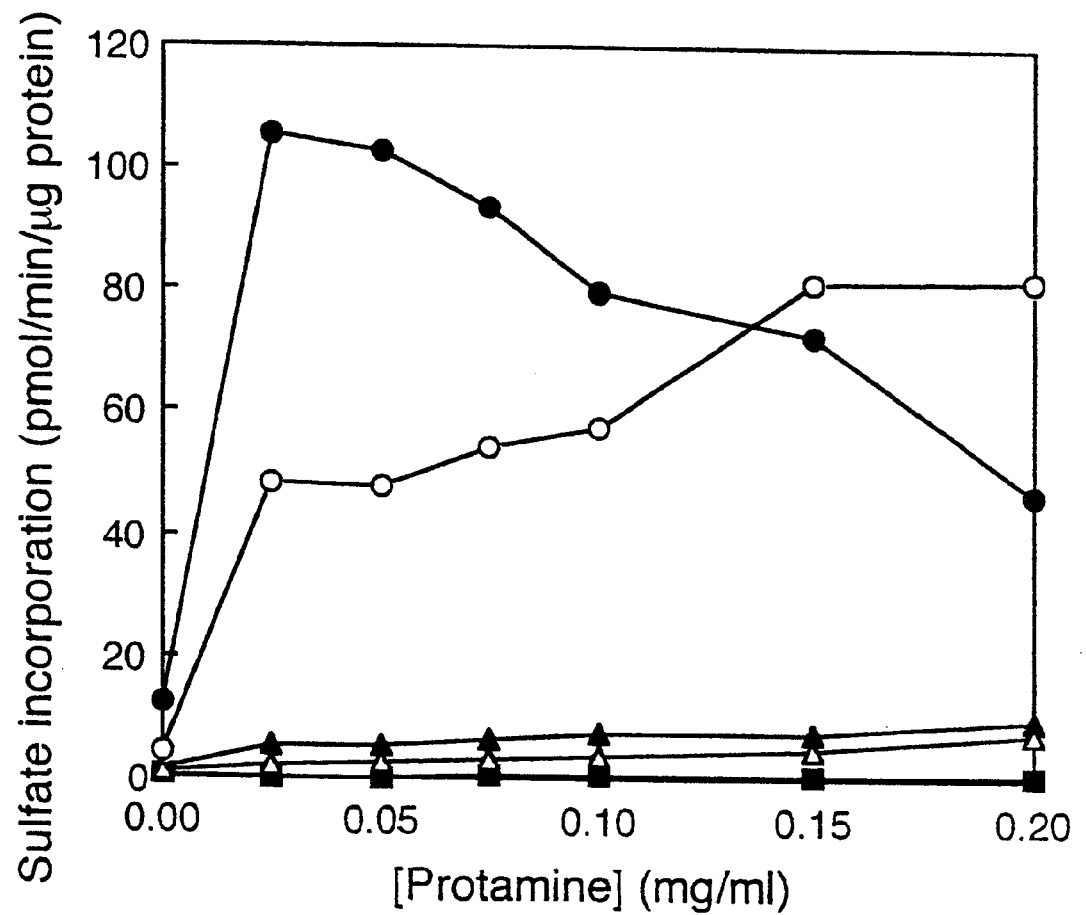
FIG. 7 shows the substrate specificity of G4ST.

To identify a sulfate group receptor, the purified G4ST was allowed to react with various glycosaminoglycans in the presence of protamine chloride in various concentrations (FIG. 7). In FIG. 7, closed circles indicate the results on chondroitin, open circles indicates the results on desulfated dermatan sulfate, closed triangles indicate the results on chondroitin sulfate A, open triangles indicates the results on chondroitin sulfate C, and closed square indicate the results on dermatan sulfate. As a result, it was demonstrated that enhancement of activity at the lowest concentration (0.25 mg/ml) was observed in the case-of chondroitin.

(6) Identification of the Sulfate Group-transferring Site of G4ST

To identify the sulfate group-transferring. site of chondroitin and desulfated dermatan sulfate, ³⁵S-labeled glycosaminoglycan obtained by sulfotransfer reaction by G4ST was digested with chondroitinase ACII (manufactured by Seikagaku Corp.) or chondroitinase ABC (manufactured by Seikagaku Corp.) and the digestion products were analyzed by HPLC (high performance liquid chromatography). $^{35}$S-Labeling was performed under the same conditions as the above-mentioned assay method for enzymatic activity except that the amount of protamine chloride was increased to 10 μg. The unsaturated disaccharides obtained by the digestion of $^{35}$S-labeled chondroitin and $^{35}$S-labeled desulfated dermatan sulfate with chondroitinase ACII or chondroitinase ABC were isolated by HPLC using a Partisil 10-SAX column (4.5 mm×25 cm: manufactured by Whatman) equiberated with $KH_2PO_4$ (35 mM). The column was eluted by concentration gradient of $KH_2PO_4$ under the conditions of a flow rate of 1 ml/minute and a column temperature of 40° C. to recover 0.5 ml of fractions.

Figure 8:
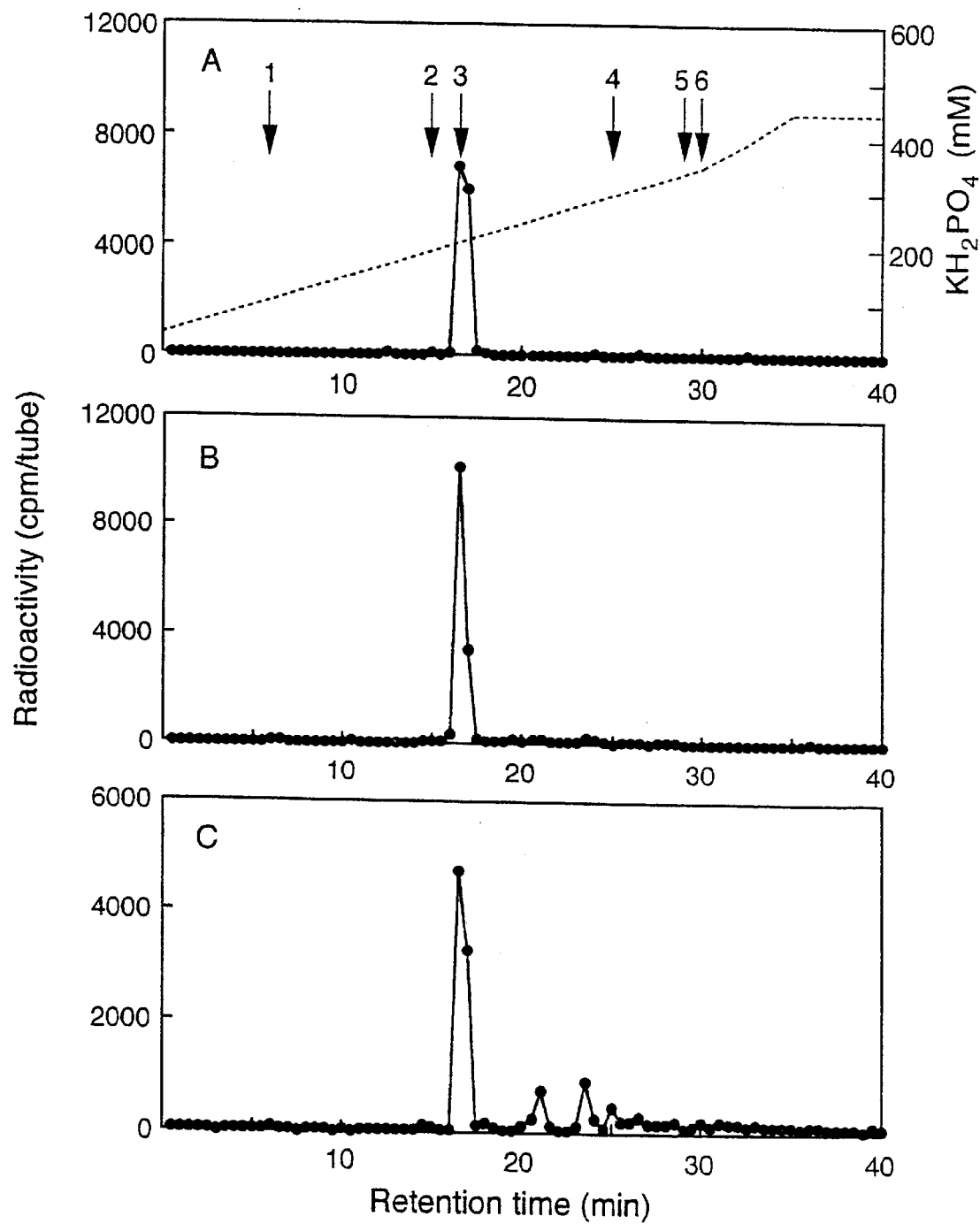
FIG. 8 shows results of chromatography of digestion products of [$^{35}$S]PAPS-labeled chondroitin sulfate and desulfated dermatan sulfate by chondroitinase ACII and chondroitinase ABC by use of a Whatman Partisil 10-SAX column.

As a result, in the case where $^{35}$S-labeled chondroitin was digested with chondroitinase ACII (FIG. 8A) and in the case where $^{35}$S-labeled desulfated dermatan sulfate was digested with chondroitinase ABC (FIG. 8B), radioactivity was detected only in the eluted fractions of ΔDi-4S. In the case $^{35}$S-labeled desulfated dermatan sulfate was digested with chondroitinase ACII, the half of all radioactivity was detected in the-eluted fractions of ΔDi-4S, other radioactivity was detected only in a smaller peak of longer elution time (FIG. 8C). In FIGS. 8A to 8C, arrows indicate respective elution positions as follows: 1; ΔDi-0S (2-acetamide-2-deoxy-3-O-(β-D-gluco-4-enepyranosyluronic acid)-D-galactose), 2; ΔDi-6S, 3; ΔDi-4S, 4; ΔDi-diS$_D$ (2-acetamide-2-deoxy-3-O-(2-O-sulfo-β-D-gluco-4-enepyranosyluronic acid)-6-O-sulfo-D-galactose), 5; ΔDi-diS$_B$ (2-acetamide-2-deoxy-3-O-(2-O-sulfo-β-D-gluco-4-enepyranosyluronic acid)-4-O-sulfo-D-galactose), and 6; ΔDi-diS$_E$ (2-acetamide-2-deoxy-3-O-(β-D-gluco-4-enepyranosyluronic acid)-4,6-bis-O-sulfo-D-galactose).

Further, a Superdex 30 gel chromatography was performed using a digestion product obtained by digesting $^{35}$S-labeled desulfated dermatan sulfate with chondroitinase ABC and chondroltinase ACII or chondroitinase ACII alone. That is, the above-mentioned digestion product was applied to a Superdex 30 16/60 high performance desalting column (manufactured by Pharmacia LKB Biotechnology) equilibrated with $NH_4HCO_3$ (0.2 M) and then eluted at a flow rate of 1 ml/minute to recover eluted fractions by every 1 ml portion.

Figure 9:
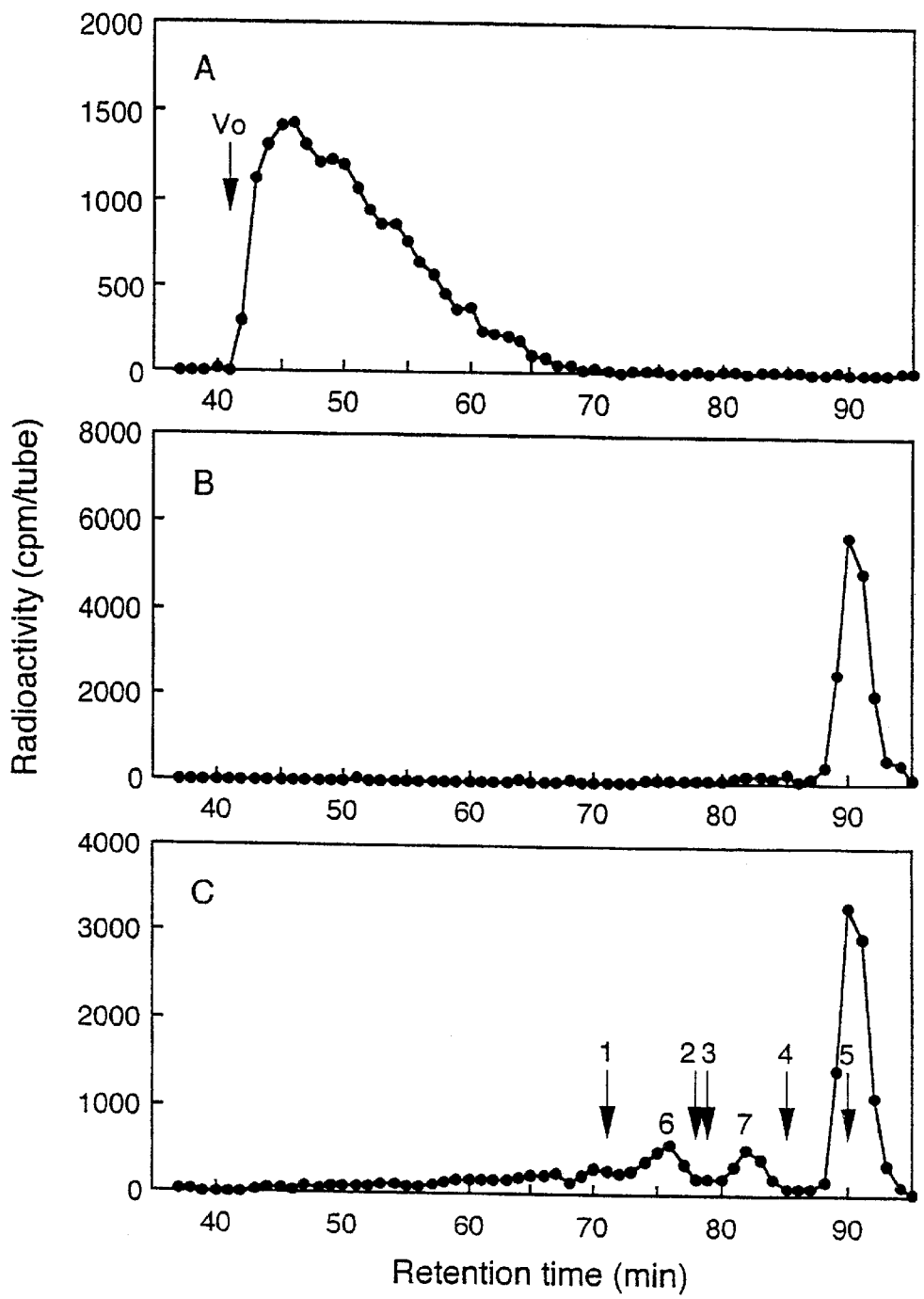
FIG. 9 shows results of chromatography of digestion products of [$^{35}$S]PAPS-labeled desulfated dermatan sulfate by chondroitinase ACII and chondroitinase ABC by use of a Superdex 30 gel column.

As a result, the radioactivity when the digestion was conducted with chondroitinase ABC and chondroitinase ACII was detected only in the eluted fraction of ΔDi-4S (FIG. 9B). About 50% of the radioactivity after the digestion with chondroitinase ACII alone was detected in the eluted fraction of ΔDi-4S (FIG. 9C). The oligosaccharides observed in FIG. 9C were demonstrated to correspond to the smaller peaks in FIG. 8C. The oligosaccharide which was eluted at 76 minutes (peak 6 in FIG. 9C) was eluted between chondroitin sulfate hexasaccharide and chondroitin hexasacchride and the oligosaccharide which eluted at 82 minutes (peak 7 in FIG. 9C) was eluted between chondroitin sulfate tetrasaccharide and chondroitin tetrasacchride. Comparison of the elution times of these oligosaccharides with the elution time of control oligosaccharides demonstrated that peaks 6 and 7 were monosulfated hexasaccharide and monosulfated tetrasaccharide, respectively. FIG. 9A illustrates the results of Superdex 30 gel chromatography of $^{35}$S-labeled desulfated dermatan sulfate before the enzymatic digestion. In FIG. 9, arrows indicate the elution positions as follows: Vo: Blue dextran; 1: chondroitin sulfate A hexasaccharide; 2: chondroitin hexasaccharide; 3: chondroitin sulfate A tetrasaccharide; 4: chondroitin tetrasaccharide; and 5: ΔDi-4S.

What is claimed is:

1. An isolated galactosaminoglycan 4-sulfotransferase from rat chondrosarcoma cells, having an activity of transferring a sulfate group from a sulfate group donor to a hydroxyl group at the C-4 position of galactosamine residue of a galactosaminoglycan, and having an optimum reaction pH of about 7.2 in imidazole hydrochloride buffer.

2. The galactosaminoglycan 4-sulfotransferase according to claim 1, wherein the galactosaminoglycan is chondroitin, chondroitin sulfate isolated from whale cartilage, chondroitin sulfate C, or desulfated dermatan sulfate.

3. The galactosaminoglycan 4-sulfotransferase according to claim 1, wherein the activity of the enzyme is enhanced by protamine or 5 mM $Ca^2$ and the activity of the enzyme is inhibited by 5 mM $Co^{2+}$.

4. The galactosaminoglycan 4-sulfotransferase according to claim 2, wherein the activity of the enzyme is enhanced by protamine or 5 mM $Ca^{2+}$ and the activity of the enzyme is inhibited by 5 mM $Co^{2+}$.

5. The galactosaminoglycan 4-sulfotransferase according to claim 1, which shows an activity of not less than 70% within a range of pH 6.3 to 7.6 compared with the activity at pH 7.2 in imidazole hydrochloride buffer.

6. The galactosaminoglycan 4-sulfotransferase according to claim 1, which has a specific activity of not less than $5.7 \times 10^{-5}$ unit/mg protein.

* * * * *